United States Patent [19]

Jessel, Jr. et al.

[11] Plant 4,229

[45] Mar. 28, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 781,864

[22] Filed: Mar. 28, 1977

[51] Int. Cl.[2] ..... A01H 5/00

[52] U.S. Cl. ..... Plt./74

[58] Field of Search ..... Plt./74

*Primary Examiner*—Robert E. Bagwill
*Attorney, Agent, or Firm*—Donald D. Jeffery

[57] ABSTRACT

A sport of Panorama differing therefrom by its orange-bronze ray floret color.

1 Drawing Figure

1

The present invention comprises a new and distinct cultivar of *Chrysanthemum morifolium,* Ramat., hereinafter referred to by the cultivar name Camino Bronze (#70309N24).

Camino bronze is a product of a planned sport induction program which had the objective of expanding the color range of the parental cultivar, Camino Pink (#70309024), disclosed in our U.S. Plant patent application filed Nov. 5, 1976, Ser. No. 739,127.

Camino Bronze was discovered and selected by William E. Duffett and Walter H. Jessel, Jr. on May 1, 1975 as one plant within a flowering block of Camino Pink in a controlled environment in Barberton, Ohio. Plants within the flowering block were derived from stock plants which had been irradiated as rooted cuttings with an x-ray source of 1800 *r* units.

The first act of asexual reproduction of Camino Bronze was accomplished when vegetative cuttings were taken from the initial selection in September, 1975 in a controlled environment in Barberton, Ohio by a technician working under formulations established and supervised by Walter H. Jessel, Jr. and William E. Duffett. Horticultural examination of selected units initiated May 1, 1975 has demonstrated that the combination of characteristics as herein disclosed for Camino Bronze are firmly fixed and are retained through successive generations of asexual reproduction.

Camino Bronze has not been observed under all possible environmental conditions. The phenotype may vary significantly with variations in environment such as temperature, light intensity, and day length. The following observations, measurements, and comparisons describe plants grown in Barberton, Ohio under greenhouse environmental conditions which approximate those generally used in commercial practice, as described in Chart A which appears at the end of the present specification. A light intensity chart of general use is shown in ASHAE Trans., Vol. 64, page 64, and reference is made thereto.

The following traits have been repeatedly observed and are determined to be basic characteristics of Camino Bronze which in combination distinguish this chrysanthemum as a new and distinct cultivar:

1. Flat capitulum form.
2. Daisy capitulum type.
3. Orange-bronze ray floret color with minimal color oxidation.
4. Uniform 9 week flowering response to photoperiodic short day control.

2

5. Medium plant height (requires 3–4 long day weeks as a single stem plant prior to short days to attain a total height as a flowering plant of 72 to 82 cm. during the flowering period October through May).
6. Diameter across face of capitulum from 60 to 80 mm. at maturity.
7. Semi-upright branching pattern.

The accompanying color photographic drawing shows typical inflorescence and foliage characteristics of Camino Bronze. Color representations are as nearly true as possible with illustrations of this type.

Of the many commercial cultivars known to the present inventors, the most similar existing cultivar in comparison to Camino Bronze is the parental cultivar, Camino Pink. Reference is made to attached Chart B which compares certain characteristics of Camino Pink with the same characteristics of Camino Bronze. As noted in Chart B, the primary distinguishing characteristic of Camino Bronze in comparison to Camino Pink is that of ray floret color. All other characteristics of Camino Bronze are similar to those same characteristics of Camino Pink.

In the following description, color references are made to The Munsell Limit Color Cascade, 1972 edition. The color values were determined between 4:30 and 5:00 P.M. on Jan. 6, 1977 under 120 foot-candle light intensity at Barberton, Ohio.

Botanical classification: *Chrysanthemum morifolium,* Ramat., cv Camino Bronze.

INFLORESCENCE

Capitulum:
- *Form.*—Flat.
- *Type.*—Daisy.
- *Diameter across face.*—60 to 80 mm.

Corolla of ray florets:
- *Color (abaxial).*—Approximately 30-10 over 28-6 to 29-6 over 28-5.
- *Color (adaxial).*—Approximately 30-11 over 28-4 to 30-10 streaked over 27-3.

Corolla of disc florets:
- *Color (immature).*—24-16 to 24-11.
- *Color (mature).*—24-12 to 26-9.

Reproductive organs:
- *Androecium.*—Present disc florets only.
- *Gynoecium.*—Present both ray and disc florets.

CHART A

| AVERAGE GREENHOUSE CHRYSANTHEMUM ENVIRONMENTS USED FOR BARBERTON, OHIO | | | | | | |
|---|---|---|---|---|---|---|
| | TEMPERATURES USED | | | | | |
| SEASON | Night | Bright Day | Cloudy Day | LIGHTING USED | BLACK CLOTH USED | SUPP $CO_2$ |
| FALL | 65° F to 56° F | 65° F to 80° F | 60° F to 75° F | 2 to 4 weeks at 3 Hours Per of 7–10 f.c. | To Sept. 15 on - 5:30 PM | From Oct. 15 |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on - 5:30 PM Off-7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on-6:00 PM Off-8:00 AM | |

CHART B

| | | COMPARISON OF COPPERAMA AND PANORAMA | | | | |
|---|---|---|---|---|---|---|
| CULTIVAR | RAY FLORET COLOR | DIAMETER ACROSS FACE OF CAPITULUM | PLANT HEIGHT | BRANCHING PATTERN | FLOWERING RESPONSE PERIOD | CAPITULUM FORM AND TYPE |
| CAMINO BRONZE | Orange Bronze | 60 to 80 mm. | Medium | Semi-upright | 9 week | Flat Daisy |
| CAMINO BRONZE | Lavender Pink | 60 to 80 mm. | Medium | Semi-upright | 9 week | Flat Daisy |

COMPARISONS MADE OF PLANTS GROWN IN A GREENHOUSE IN BARBERTON, OHIO UNDER ENVIRONMENTAL CONDITIONS AS DESCRIBED IN CHART A.

PLANT

General appearance: semi-upright branching pattern; medium height.

Foliage:

*Color (abaxial)*.—19-15 to 21-15.

*Color (adaxial)*.—21-15 to 21-14.

We claim:

1. A new and distinct cultivar of *Chrysanthemum morifolium,* Ramat, known by the cultivar name Camino Bronze and particularly characterized as to uniqueness by the combined characteristics of flat capitulum form, daisy capitulum type, orange-bronze ray floret color with minimal color oxidation, uniform 9 week flowering response to photoperiodic shortday control, medium plant height, diameter across face of capitulum from 60 to 80 mm. at maturity, and semi-upright branching pattern.

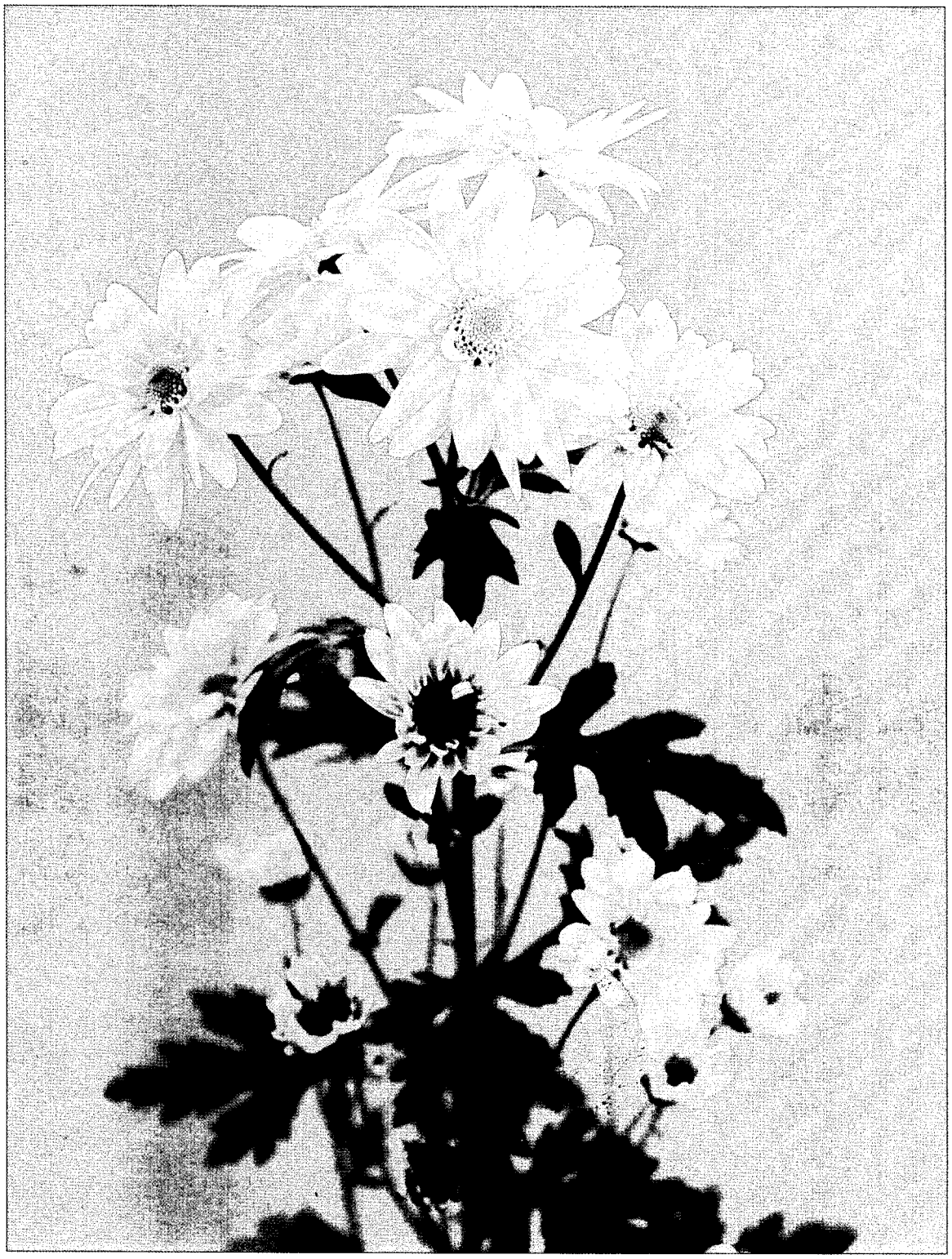

* * * * *